United States Patent [19]

Misaki et al.

[11] Patent Number: 4,639,516
[45] Date of Patent: Jan. 27, 1987

[54] POLYSACCHARIDE POLYOL

[75] Inventors: Akira Misaki, Osaka; Yoshiaki Sone, Sennan; Takao Kato, Shinnanyo, all of Japan

[73] Assignee: Toyo Soda Manufacturing Co., Ltd., Shinnanyo, Japan

[21] Appl. No.: 587,475

[22] Filed: Mar. 8, 1984

[30] Foreign Application Priority Data

Mar. 9, 1983 [JP] Japan .................................. 58-37486

[51] Int. Cl.4 ............................................. C08B 37/00
[52] U.S. Cl. ...................................... 536/123; 536/1.1
[58] Field of Search ................. 536/1.1, 123, 124, 127

[56] References Cited

U.S. PATENT DOCUMENTS 3,691,153 9/1972 Vemuri ............................... 536/114
4,454,289 6/1984 Nakajima et al. ...................... 536/1.1
4,511,559 4/1985 Szendrei et al. ...................... 536/127

OTHER PUBLICATIONS

Migrdichian, *Organic Synthesis*, vol. 1, pp. 61-62, 1957.
Chemical Abstracts, vol. 101, p. 56, No. 101:33216g, 1984.

Primary Examiner—Johnnie R. Brown
Assistant Examiner—Elli Peselev
Attorney, Agent, or Firm—Cushman, Darby & Cushman

[57] ABSTRACT

Described is a polysaccharide polyol derived from *Volvariella volvacea*, which is comprised of the following three types of recurring units.

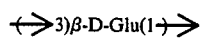

I

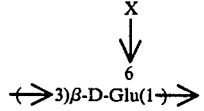

II

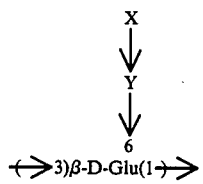

III wherein D-Glu is D-glucopyranosyl residue, each number represents the linkage position, X is $HOCH_2CH(CH_2OH)$—O—$CH(CH_2OH)$—O—[Formula A] or D-glucopyranosyl and Y is —$CH_2$—$CH(CH_2OH)$—O—$CH(CH_2OH)$—O— or D-glucopyranosyl, at least a part of X in the recurring units II and III is that of formula A, and, the average number of III is about 4–12 and the average number of the sum II and III is about 16–23, per 100 of the sum of I, II and III. The polysaccharide is prepared by extracting *Volvariella volvacea* with an aqueous alkali solution and oxidizing and then reducing the soluble fraction to cut parts of C—C bonds of side chains. The polysaccharide is useful and an anti-tumor agent.

1 Claim, 2 Drawing Figures

POLYSACCHARIDE POLYOL

BACKGROUND OF THE INVENTION (1) Field of the Invention

This invention relates to a polysaccharide polyol derived from *Volvariella volvacea*, a process for the preparation of this polyscaccharide polyol and an anti-tumor agent comprising this polysaccharide polyol as an active component.

(2) Description of the Prior Art

It is known that certain polysaccharides have an anti-tumor activity, but the relation between the structure and the anti-tumor activity has not been elucidated.

It also is known that polysaccharides having an anti-tumor activity can be obtained by oxidizing and reducing polysaccharides originating from certain fungi to convert them to polyols. For example, Japanese Unexamined Patent Publications No. 55-25409 and No. 56-34701 teach that when polysaccharides produced by *Auricularia auricula-judae* and a microorganism belonging to the genus Pestalotia are subjected to the above treatment, polysaccharides having an anti-tumor activity are obtained. Also in these polysaccharides, however, the relation between the structure of the starting polysaccharide or its polyol and the anti-tumor activity has not sufficiently been elucidated.

We already found that a polysaccharide obtained by alkali extraction of *Volvariella volvacea* has a strong anti-tumor activity (see Japanese Patent Publication No. 57-162121). However, if this polysaccharide is dried, it becomes hardly soluble in water under neutral conditions, and it cannot be deemed that the adaptability of this polysaccharide as an anti-tumor agent to the clinical treatment is sufficient.

We made research with a view to improving the water solubility of the polysaccharide disclosed in Japanese Patent Publication No. 57-162121 under neutral conditions without degradation of the anti-tumor activity, and as the result, it was found that if this polysaccharide is oxidized with an oxidant, especially periodic acid or a water-soluble salt thereof, and is then reduced, the water-solubility of the treated polysaccharide under neutral conditions is highly improved over that of the untreated polysaccharide and the anti-tumor activity is enhanced.

SUMMARY OF THE INVENTION

It is a primary object of the present invention to provide a polysaccharide polyol having an adjustable improved water solubility and an enhanced anti-tumor activity, which is prepared by oxidizing an alkali-soluble polysaccharide contained in *Volvariella volvacea* with an oxidant, especially periodic acid or a watersoluble salt thereof, and reducing the oxidized polysaccharide.

Other objects and advantages of the present invention will be apparent from the following description.

In one aspect of the present invention, there is provided a polysaccharide polyol derived from *Volvariella volvacea*, which consists essentially of first recurring units represented by the following formula (I):

wherein D-Glu represents a D-glucopyranose residue $\beta$ represents the linkage mode and each number represents the linkage position, second recurring units represented by the following formula (II):

wherein D-Glu, $\beta$ and each number are defined above, and X represents a group represented by the following formula:

or a D-glucopyranosyl group represented by the following formula:

and third recurring units represented by the following formula (III):

wherein D-Glu, $\beta$ and each number are defined above, and Y represents a group represented by the following formula (C):

or a D-glucopyranosyl residue represented by the following formula (D):

in each formula, X being linked to the carbon atom to which (P) is attached and the group being linked to the glucopyranosyl residue through the oxygen atom to which (Q) is attached,
wherein at least a part of X in the second recurring units and/or the third recurring units is a group represented by the following formula (A):

the average number of the third recurring units is about 4 to about 12 per 100 of the sum of the first, second and third recurring units, and the average number of the sum of the second and third recurring units is about 16 to about 33, especially about 16 to 23, per 100 of the sum of the first, second and third recurring units.

In another aspect of the present invention, there is provided a process for the preparation of the above-mentioned polysaccharide derived from *Volvariella volvacea*, which comprises extracting *Volvariella volvacea* with an aqueous alkaline solution and oxidizing and then reducing the obtained soluble fraction to cut parts of carbon-to-carbon linkages in the side chains.

In still another aspect of the present invention, there is provided an anti-tumor agent comprising as an active component the above-mentioned polysaccharide polyol derived from *Volvariella volvacea*.

DESCRIPTION OF THE PREFERRED EMBODIMENTS

The physical and chemical properties of the polysaccharide polyol of the present invention will now be described.

(1) Solubility:
The polysaccharide polyol is soluble in water, physiological saline solution, an aqueous alkali solution and dimethylsulfoxide, but is substantially insoluble in methanol, ethanol, n-butanol, acetone, benzene, toluene, ethyl acetate, propylene glycol and pyridine.

(2) Optical Rotation:
The specific rotatory power of the polysaccharide polyol of the present invention in an aqueous 0.5N solution of sodium hydroxide (0.5%) is as follows:
$[\alpha]_D^{25}$: about $+22.4°$ (3) Elementary Analysis:
The elementary analysis values of a sufficiently dried sample are as follows:
C: 43 to 44.5%
H: 5.8 to 6.3%
N and S are below the detection limit.

(4) Molecular Weight:
In the gel permeation high pressure liquid chromatography using as the mobile phase a tris-hydrochloride buffer solution having a concentration of 0.1 mole/l and a pH value of 8.6 (varied according to conditions), the polysaccharide polyol is eluted into a fraction having a molecular weight of about 70,000 to about 2,800,000, especially about 70,000 to about 800,000. The optional viscosity-reducing treatment can reduce the molecular weight within the range.

(5) Constituent Saccharides:
Identification and determination are carried out by high pressure liquid chromatography (mobile phase: $CH_3CN/H_2O=75/25$, column: LS-450K supplied by Toyo Soda Co.) after hydrolysis of the polysaccharide polyol of the present invention with formic acid and sulfuric acid or with sulfuric acid, paper chromatography (developing solvent: butanol/pyridine/water=6/4/3, color reagent: solution of silver nitrate), and gas chromatography (column: Thermon-3000 and ECNSS-N) after derivation to alditol acetate.

(A) When the polysaccharide polyol is completely hydrolyzed, glucose, glycerol and glycolaldehyde are formed.

(B) When the polysaccharide polyol of the present invention is methylated according to Hakomori method and hydrolyzed and then the hydrolyzed product is analyzed by gas chromatography directly or after derivation to alditol acetate, 2,4,6-tri-0-methylglucose is detected as the main component and 2,4-di-0-methylglucose and 1,3-di-0-methylglycerol are detected. Furthermore, very small amounts of 2,3,4,6-tetra-0-methylglucose and 2,3,4-tri-0-methylglucose are detected or not detected in some cases.

(C) When the glucan of the present invention is subjected to mild hydrolysis with an acid, a white precipitate is formed. When the water-soluble fraction is analyzed by high pressure liquid chromatography, the presence of glycerol is confirmed. When this white precipitate is methylated and hydrolyzed and then the hydrolyzed product is analyzed by gas chromatography directly or after derivation to alditol acetate, only 2,4,6-tri-0-methylglucose is detected as the main component and in addition, a trace of 2,3,4,6-tetra-0-methylglucose is detected.

Accordingly, it is concluded that the main chain of the polysaccharide polyol of the present invention consists substantially of β-1,3-linked glucose and the main chain attached with side chains composed mainly of a single glucose residue or a group formed by cutting a part of the carbon-to-carbon linkages in the glucose residue and converting it to a polyol, the side chains are bonded through β-linkages to the 6-positions of the β-1,3-linked glucose residues of the main chain at a ratio of one side chain per 3 to 6, especially 4 to 6 of β-1,3-linked glucose linkages, and about 1/3 to about 1/10 of the side chains consist of two β-1,6-linked glucose residues or groups formed by cutting parts of the carbon-to-carbon linkages in said glucose residues and converting them to polyols.

From the foregoing results and the structure of the parent polysaccharide derived from *Volvariella volvacea* described hereinafter, the polysaccharide polyol of the present invention can be identified as a polysaccharide polyol derived from *Volvariella volvacea*, which consists essentially of the above-mentioned first, second and third recurring units.

It is preferred that the sum of group X represented by the formula (A) and group Y represented by the formula (C) in the recurring units represented by the formulae (II) and (III) in the polysaccharide polyol of the present invention be larger than ¼ of the sum of the groups X and Y represented by the formulae (A), (B), (C) and (D).

The ratios of the sum of the groups of the formulae (A) and (C) and the sum of the groups of the formulae (B) and (D) to the β-1,3-glucopyranose units of the main chain can be calculated from the amount of periodic acid consumed and the amount of formic acid formed when the polysaccharide polyol of the present invention is completely oxidized with periodic acid and also from the amounts of the glycerol and glucose determined when the polysaccharide of the present invention is completely hydrolyzed.

The above-mentioned polysaccharide polyol of the present invention is prepared by extracting *Volvariella volvacea* with an aqueous alkaline solution, oxidizing the obtained soluble fraction and reducing the oxidation product to the corresponding polysaccharide polyalcohol.

Either a fruit body or mycelium of *Volariella volvacea* may be used as the starting material in the present invention. The starting material may be raw or a dried product. In order to increase the extraction efficiency, it is preferred that the starting material is finely crushed before the extraction.

An alkali metal hydroxide such as sodium hydroxide or potassium hydroxide may be used for the aqueous alkaline solution used for the extraction. An aqueous sodium hydroxide solution is especially preferred.

The alkali concentration is not particularly critical, but it is ordinarily preferred that the alkali metal hydroxide be used in the form of an aqueous solution having a normality of about 0.1 to about 3N.

The amount of the aqueous alkaline solution used for one extraction is ordinarily about 5 to about 100 times the amount of the dry starting material based on the weight. If the amount of the aqueous alkaline solution is too small, the extraction efficiency is low, and if the amount of the aqueous alkaline solution is too large, the post treatment becomes troublesome.

In order to prevent alteration of the chemical properties of the polysaccharide such as decomposition or peroxidation at this extraction step, it is preferred that the extraction be carried out in an atmosphere of an inert gas such as nitrogen. The extraction may be carried out in the presence of a reducing agent such as sodium borohydride.

The extraction temperature is not particularly critical, but it is ordinarily preferred that the extraction temperature be not higher than about 30° C. The reason is that the extraction is carried out under ordinary hot alkali extraction conditions, for example, at about 60° to about 80° C., polysaccharides having many more branches are further extracted. The extraction operation may be performed repeatedly.

The parent polysachharide obtained by extracting Volvariella volvacea in the process of the present invention is not extracted with a solvent such as water or an alcohol. Accordingly, it is preferred that before the step of extraction with the aqueous alkaline solution, impurities be removed by washing with a solvent such as water, hot water, a buffer solution, an alcohol or a mixture thereof. By this treatment, proteins, mannogalactanes and glycogen-like polysaccharides acting as impurities at the aqueous alkaline solution extraction step can be substantially removed.

After the extraction, the aqueous alkalline extract is neutralized with an acid such as hydrochloric acid or acetic acid. At this stage, the intended intermediate polysaccharide is dissolved in the salt solution. Then, a quaternary ammonium salt such as cetyl pyridinium chloride may be added to the solution to precipitate acidic substances which may be accompanied with, as insoluble solids, followed by the solid removal carried out by customary separation means such as filtration or centrifugal separation. The thus resulting liquor is dialyzed directly or after concentration and the dialyzate is dried to obtain an intermediate polysaccharide. Alternately, the liquor is optionally concentrated and a precipitating agent such as an alcohol or acetone is added thereto, and the obtained precipitate is optionally dialyzed to water and is dried, whereby the parent polysaccharide is obtained in the solid form. Appropriate drying means such as reduced pressure drying, freeze-drying or spray drying may be adopted. If desired, parts of these steps may be omitted, and the subsequent oxidation treatment may directly be carried out.

The thus-obtained parent polysaccharide is a polysaccharide consisting essentially of first recurring units represented by the following formula (I):

wherein Glu stands for a glucopyranosyl residue and each number represents the linkage
position, second recurring units represented by the following formula (IV):

wherein Glu and each number are as defined above, and third recurring units represented by the following formula V:

wherein Glu and each number are as defined above, wherein the average number of the third recurring units [formula (V)]is about 4 to about 12 per 100 of the sum of the first recurring units [formula (I)], the second recurring units [formula (IV)]and the third recurring units [formula (V)]and the average number of the sum of the second recurring units [formula (IV)]and the third recurring units [formula (V)]is about 16 to about 33, especially about 16 to about 23 per 100 of the sum of the first, second and third recurring units.

The physical and chemical properties of this polysaccharide will now be described.

(1) Solubility:

The polysaccharide is soluble an aqueous alkali solution and dimethylsulfoxide but is substantially insoluble in methanol, ethanol, n-butanol, acetone, benzene, toluene, ethyl acetate, propylene glycol and pyridine. The polysaccharide, when dried up, is hardly soluble in water, but it is partly solubilized in water by a treatment such as ultrasonic irradiation. The polysaccharide is slightly soluble in a salt solution. When the polysaccharide is dissolved in an aqueous alkali solution in a low concentration and the solution is then neutralized, the polysaccharide is kept dissolved.

(2) Optical Rotation:

The specific rotatory power of the polysaccharide in an aqueous 0.5N sodium hydroxide solution (0.5%) is as follows:

$[\alpha]_D^{25}$: about $-12°$ (3) Elementary Analysis Values:

When the polysaccharide is carefully dried up, values close to the values calculated from $C_nH_{2n}O_n$ are obtained. However, a small amount of water is ordinarily contained, and the following result may be obtained.

C: 43–45%

H: 5.6–6.4%

N: below detection limit

Halogens and sulfur are not detected.

Figure 1:
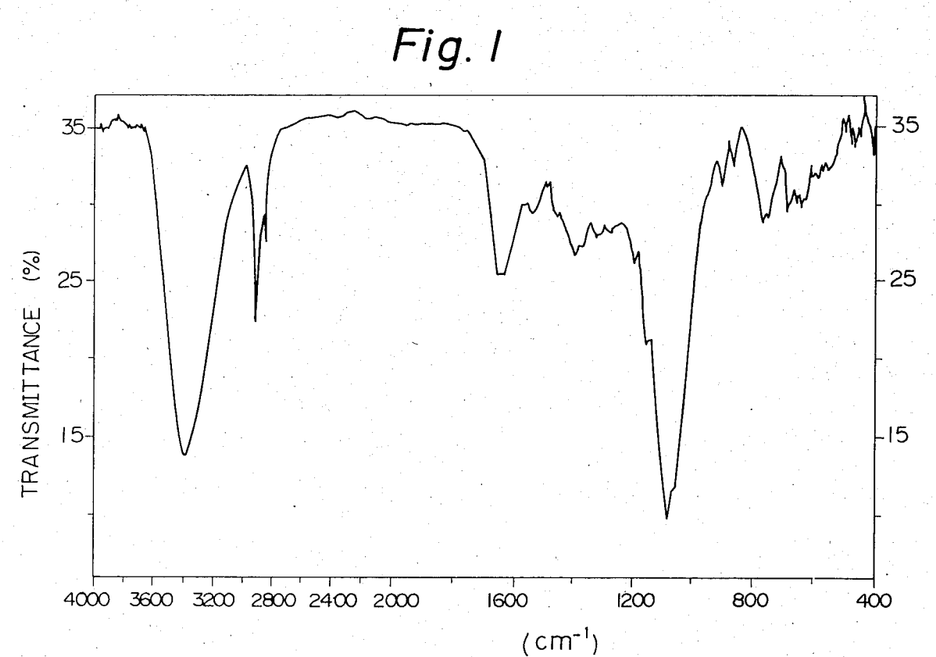
FIG. 1 shows an infrared absorption spectrum of an parent polysaccharide prepared by the alkali extraction of *Volvariella volvacea* in Example 1; and, FIG. 2 shows an infrared absorption spectrum of a polysaccharide polyol of the present invention prepared in Example 1.

(4) Infrared Absorption Analysis:

The infrared absorption spectrum obtained by the KBr tablet method is shown in FIG. 1. The absorption at 896 cm$^{-1}$ is attributable to the β-linkage of the D-glucose residue.

(5) $C^{13}$-NMR Analysis:

Peaks are observed at δ values of 103.6, 86.8, 76.9, 75.2, 74.2, 73.3, 70.7, 69.0 and 61.4 ppm.

(6) Color Development Reaction:

Anthrone reaction: positive

Ninhydrin reaction: negative

Dische's carbozole reaction: negative (7) Molecular Weight:

The polysaccharide is eluted in a fraction having a molecular weight of about 300,000 to about 2,800,000, especially about 300,000 to about 800,000 in gel permeation high speed liquid chromatography using as the mobile phase a tris-hydrochloride buffer solution having a concentration of 0.1 mole/l and a pH value of 8.6.

(8) Reaction with Cetyl Pyridinium Chloride:

In an aqueous solution, the polysaccharide does not form a precipitate with cetyl pyridinium chloride.

(9) Constituent Saccharides:

When the polysacchardie is identified by paper chromatography after hydrolysis in an aqueous 1N sulfuric acid solution at 100° C. or by gas chromatography after derivation to alditol acetate, only glucose is detected.

(10) Linking Mode:

At the methylation analysis, the polysaccharide gives 1 mole of 2,3,4,6-tetra-0-methylglucose, about 2.7 to about 5.0, especially about 3.7 to about 5.0 moles of 2,4,6-tri-0-methylglucose, about 0.10 to about 0.35, especially about 0.30 to about 0.35 mole of 2,3,4-tris-0-methylglucose and about 0.7 to about 1.3 moles of 2,4-di-0-methylglucose.

When the polysaccharide is subjected to enzymatic decomposition using an exo-type β-1,3-glucanase, glucose and gentiobiose are formed.

When the polysaccharide is sufficiently oxidized with sodium metaperiodate, reduced with sodium borohydride and then hydrolyzed under mild conditions, for example, at 80° to 100° C. for 1 to 2 hours with 0.1 or 0.2N sulfuric acid, a linear β-1,3-glucan, from which glucose groups corresponding to the side chains have been removed, is obtained. Methylation analysis of this glucan gives 2,4,6-tri-0-methylglucose and a trace of 2,3,4,6-tetra-0-methylglucose. When this β-1,3-glucan is enzymatically decomposed with an exo-type β-1,3-glucanase, only glucose is formed.

Accordingly, the main chain of this polysaccharide consists substantially of β-1,3-linked glucose residues.

It is therefore construed that the main chain of this polysaccharide consists of continuous β-1,3-glucoside linkages and the main chain contains side chains composed mainly of a single glucose residue, the side chains are covalently joined through β-linkages to the 6-positions of the β-1,3-linked glucose linkages of the main chain at a ratio of one side chain per 3 to 6, especially 4 to 6 of β-1,3-glucose linkages, and about ⅓ to about 1/10 of the side chains consist of β-1,6-linked two glucose residues. Accordingly, it is deemed that the basic structure of this polysaccharide consists of the recurring units represented by the above-mentioned general formulae.

From the aforementioned facts, it is seen that the parent polysaccharide formed in the midway of the process of the present invention has a lower branching frequency than those of known branched β-1,3-glucan obtained from a fruit body of *Auricularia auricula-judae, scleroglucan*, and schizophylan, and the polysaccharide contains s slight portions of branches consisting of at least two glucose residues connected in series through β-1,6-linkages.

This polysaccharide is a substance disclosed in the specification of Japanese Patent Application No. 57-157058.

The thus-obtained parent polysaccharide is oxidized with an oxidant, especially periodic acid or a water-soluble salt thereof, and is then subjected to a reducing treatment. If desired, a viscosity-reducing treatment such as an ultrasonic irradiation treatment may be carried out at any stage.

An oxidant capable of selectively oxidizing the carbon-to-carbon linkage adjacent hydroxyl groups is used in the process of the present invention. For example, periodic acid and salts thereof, especially sodium metaperiodate and potassium metaperiodate, are preferably used. A buffer solution having a pH value of 3 to 8 may be used as the solvent for the oxidation reaction. Ordinarily, distilled water is convenient. The concentration of the oxidant is not particularly critical, but is preferred that the concentration of the oxidant be 0.01 to 0.2 mole/l, especially 0.02 to 0.1 mole/l. The oxidant is used in such an amount that the intended ring opening degree is given. It is ordinarily preferred that the oxidant be used in an amount of about 0.02 to about 2 moles per mole of glucosyl residue of the starting polysaccharide. If the amount of the oxidant is too small, the conversion of the polysaccharide to the intended water-soluble modified polysaccharide is insufficient, but even if the oxidant is used in a too large amount, an effect exceeding the effect attained by use of an appropriate amount of the oxidant cannot be attained. It is sufficient if the solvent is used in such an amount that the starting polysaccharide is fully immersed in the solvent and the mixture is sufficiently stirred. It is ordinarily preferred that the solvent be used in an amount of 10 to 500 parts per part of the starting polysaccharide.

The oxidation reaction is preferably carried out at room temperature or a lower temperature, and the oxidation reaction may be carried out in an atmosphere of an inert gas. Ordinarily, the oxidation reaction is conducted in the dark place.

By the above-mentioned oxidation treatment, the $\beta$-1,3-glucopyranosyl residue constituting the main chain of the intermediate polysaccharide are not oxidized, but only the glucopyranosyl residue at the positions X and Y in the recurring units represented by the formulae (IV) and (V) are oxidized.

The step of decomposing the remaining oxidant by ethylene glycol or glycerol after completion of the oxidation reaction is not particularly indispensable, but is a preferred step.

In the subsequent reduction reaction, a water-soluble reducing agent is preferably used. For example, sodium borohydride (NaBH$_4$) can be mentioned. Sodium borohydride is especially preferred. The liquid reaction mixture may be made slightly alkaline by addition of sodium bicarbonate or the like before the reduction reaction. The amount of the reducing agent varies according to the method of treating the liquid reaction mixture obtained by the oxidation reaction. In the case where the oxidant is decomposed by ethylene glycol and the pH value is adjusted to 8 by sodium bicarbonate, the reducing agent is used in an amount at least about 1.2 times the stoichiometric amount. An aqueous solvent is preferably used for the reduction reaction, and it is preferred that the solvent be used in an amount 100 to 1000 times the amount of the starting polysaccharide. The reduction may be carried out at room temperature with stirring. It is sufficient if the reduction reaction is conducted for about 1 day.

By the above-mentioned oxidation treatment and reduction treatment, the starting polysaccharide, which is hardly soluble in water, is converted to a water-soluble polysaccharide, and the formed polysaccharide is dissolved in the reaction liquid.

In the case where sodium borohydride is used as the reducing agent, there may be adopted a method in which a mineral acid or organic acid is added to the reaction liquid after completion of the reduction reaction to make the reaction liquid slightly acidic and decompose the remaining sodium boron hydride. In the case where a water-insoluble residue is left even after the reduction reaction, the residue may be removed by a customary solid-liquid separation method such as centrifugal separation.

The so-obtained solution containing the water-soluble polysaccharidep polyol may be dialyzed into distilled water as it is or after it has been concentrated under reduced pressure.

There may also be adopted a method in which a water-soluble poor solvent such as methyl alcohol or acetone is added to the polysaccharide polyol containing solution before or after concentration to precipitate the intended polysaccharide, the precipitate is collected by customary means such as centrifugal separation, the precipitate is dissolved in distilled water and the dialysis is effected. Of course, this purification method may be conducted repeatedly. It is ordinarily sufficient if the dialysis is conducted for 2 to 5 days.

The obtained internal liquid is converted to a solid by customary means such as freeze drying or spray drying. In the case where the precipitating operation is carried out by adding a poor solvent after the dialysis, the precipitate may be washed sufficiently with the solvent used for the precipitating operation and be subjected to drying under reduced pressure.

The viscosity-reducing treatment such as an ultrasonic irradiation treatment or a $\beta$-1,3-glucan decomposing enzyme treatment may be carried out at any of the foregoing steps.

The thus-obtained polysaccharide polyol of the present invention is highly improved over the above-mentioned parent polysaccharide in the water solubility under neutral conditions. Furthermore, the anti-tumor activity of the polysaccharide polyol of the present invention is enhanced.

The polysaccharide polyol of the present invention obtained from the polysaccharide derived from *Volvariella volvacea* is in agreement with the above-mentioned two known polysaccharide polyol derived from *Auricularia auricula-judae* and a microorganism belonging to the genus Pestalotia in the point where the main chain is composed of $\beta$-1,3-glucan, but this polysaccharide is characteristic over the two known polysaccharides in the point where the branching degree is very low.

The polysaccharide polyol of this invention has a very high antitumor activity, while it shows very low toxicity in mammalia, for example, values larger than 1,000 mg/Kg in LD$_{50}$ when administered intraperitoneally in mice.

The polysaccharide polyol of this invention can be administered as known anti-tumor polysaccharides in a conventional way such as intravenous, intramusclar or subcutaneous injection after it is dissolved or dispersed in a physiologically acceptable medium.

The present invention will now be described in more detail with reference to the following Examples.

EXAMPLE 1

In 1 liter of a 0.1M phosphate buffer solution having a pH value of 7.0 and containing 0.9% sodium chloride was immersed 100 g of an air-dried fruit body of *Volvariella volvacea* overnight, and the fruit body was pulverized by a mixer and a homogenizer. Then, 2 liters of the same phosphate buffer solution as described above was added and the mixture was stirred for 4 hours and then subjected to centrifugal separation. The obtained solid was added to 3 liters of the same phosphate buffer solution as described above and dispersed by a homogenizer. The mixture was stirred for 4 hours and was subjected to centrifugal separation to obtain a precipitate. This precipitate was dispersed in 3 liters of water and the dispersion was heated at 120° C. for 30 minutes in an autoclave. The mixture was cooled and subjected to centrifugal separation to obtain a precipitate. This hot water extraction treatment was further conducted 4 times, and the water-soluble fraction was thus extracted and removed substantially completely.

The thus-obtained water-insoluble fraction was dispersed in 3 liters of an aqueous 1N sodium hydroxide solution having 5 g of sodium boron hydride dissolved therein. The dispersion was stirred at 25° C. for 4 hours in a nitrogen current and was then subjected to centrifugal separation. The obtained precipitate was extracted with an aqueous 1N sodium hydroxide solution again. Both the sodium hydroxide extracts were combined, and the combined solution was nuetralized with concentrated hydrochloric acid to adjust the pH value to 6.5.

An aqueous cetyl pyridinium chloride solution (10% concentration) was added to the thus-obtained extract with stirring until a new precipitate was not formed any more by the addition, and centrifugal separation was carried out under 10,000 G for 30 minutes, and the formed precipitate was removed. The supernatant was mixed with methanol in the same volume as that of the supernatant and the mixture was stirred to precipitate a polysaccharide. The precipitate was added to 500 ml of distilled water and dispersed by a homogenizing mixer, and the dialysis was carried out in running water for 5 days.

The internal liquid was freeze-dried to obtain 13.0 g of an parent polysaccharide.

Elementary Analysis Values:
C: 44.03%
H: 6.05%
N: below detection limit

Specific Rotatory Power:
$[\alpha]_D^{25}$: $-12°$ (in an aqueous 0.5N sodium hydroxide solution having a concentration of 0.5%)

Infrared Absorption Spectrum:
The Fourier transform infrared absorption spectrum by the KBr tablet method is shown in FIG. 1.

Molecular Weight:
The polysaccharide was eluted at the position of the retention time of a molecular weight of about 680,000 in gel permeation high pressure liquid chromatography using as the mobile phase a 0.1M tris-hydrochloride buffer solution having a pH value of 8.6 and a column G5000 PW supplied by Toyo Soda Co.

$C^{13}$-NMR Analysis, Color Development Reaction and Reaction with Cetyl Pyridinium Chloride:
The same results as described hereinbefore were obtained.

Constituent Saccharides and Linking Mode:
The obtained polysaccharide was methylated and then hydrolyzed. The obtained methylated saccharides were converted to alditol acetates and analyzed by gas chromatography. It was found that the methylated saccharides comprised 1 mole of 2,3,4,6-tetra-0-methyl-glucose, 3.76 moles of 2,4,6-tri-0-methylglucose, 0.33 mole of 2,3,4-tri-0-methylglucose and 1.01 moles of 2,4-di-methylglucose.

Separately, this polysaccharide was enzymatically decomposed by an exo-type $\beta$-1,3-glucanase. Glucose and gentiobiose were obtained at a molar ratio of 1/0.177.

This polysaccharide was sufficiently oxidized with sodium metaperiodate and then reduced with sodium borohydride. When the reduction product was hydrolyzed in 0.1N sulfuric acid at 100° C. for 2 hours, a precipitate of a linear glucan, from which glucose groups corresponding to the side chains had been removed, was obtained. When this precipitate was subjected to the methylation analysis in the same manner as described above, 2,4,6-tri-0-methylglucose and a trace amount of 2,3,4,6-tetra-0-methylglucose were obtained.

When the above precipitate was enzymatically decomposed with an exo-type $\beta$-1,3-glucanase, only glucose was formed.

Accordingly, it was confirmed that the obtained polysaccharide comprised the recurring units represented by the above-mentioned formulae (I), (IV) and (V), the number of the recurring units of the formula (V) was 7 per 100 of the sum of these recurring units of the formulae (I), (IV) and (V) and the number of the sum of the recurring units of the formulae (IV) and (V) was 21 per 100 of the sum of the recurring units of the formulae (I), (IV) and (V).

Then, 2 g of the thus-prepared parent polysaccharide was added to 300 ml of distilled water and the mixture was sufficiently stirred. Then, 1.2 g of sodium metaperiodate was added to the mixture, and the mixture was stirred at 10° C. under insulation of light for 10 days to effect reaction. Then, 1 ml of ethylene glycol was added to the reaction mixture, and the mixture was stirred for 3 hours. The reaction mixture was subjected to centrifugal separation under 8,000 G for 30 minutes. The supernatant was removed and then the solid was recovered. The solid was transferred into 500 ml of distilled water and dispersed by a disperser. Then, 0.25 g of sodium borohydride was added to the dispersion, and the dispersion was stirred at room temperature for one day. Then, the reaction mixture was subjected to a centrifugal separation. A small amount of acetic acid was added to the supernatant to adjust the pH value to 6.5. The resulting liquor was mixed with methanol in an amount 2 times the amount of the neutralized liquor, and the mixture was stirred and then subjected to centrifugal separation. The supernatant was removed, and the obtained precipitate was dissolved in 300 ml of distilled water and dialysis was conducted for 5 days. The internal liquid was freeze-dried to obtain 1.7 g of a white intended polysaccharide polyol.

The properties of the so-obtained polysaccharide polyol were as described below.

The same analysis methods as used for the parent polysaccharide were adopted.

Incidentally, in the subsequent Examples, the same analysis methods were adopted.

Elementary Analysis Values:
C: 43.8%
H: 6.1%

Figure 2:
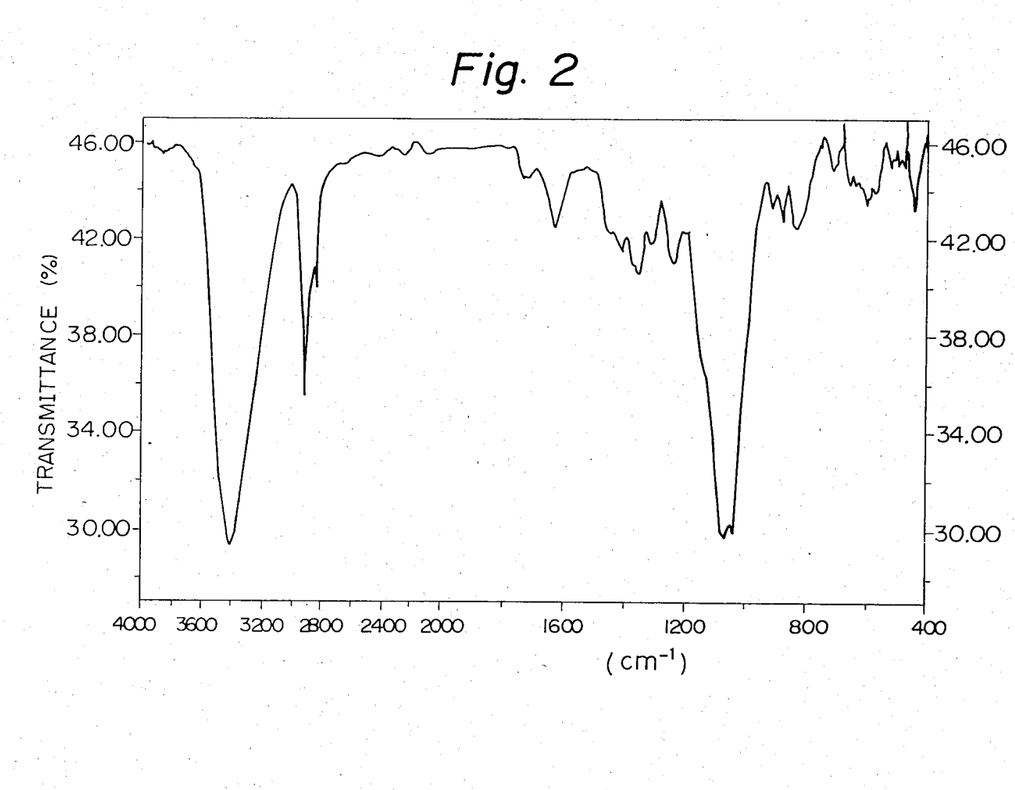

Infrared Absorption Spectrum:
The Fourier transform infrared absorption spectrum by the KBr tablet method is shown in FIG. 2.

Molecular Weight:
The polysaccharide polyol was eluted at the position of the retention time of a molecular weight of about 650,000 in gel permeation high speed liquid chromatography using as the mobile phase a 0.1M trishydrochloride buffer solution having a pH value of 8.6 and a column G5000 PW supplied by Toyo Soda Co.

Structure:
The polysaccharide polyol consisted of the first, second and third recurring units of the formulae (I), (II) and (III), and per 100 of the sum of the first, second and third recurring units, the number of the third recurring units was about 7, the number of the sum of the second and third recurring units was 21, the number of the sum of the groups of the formulae (A) and (C) was about 24 and the number of the sum of the formulae (B) and (D) was about 4.

EXAMPLE 2

The oxidation treatment and subsequent treatments were carried out by using 2 g of the parent polysaccharide prepared in Example 1 in the same manner as described in Example 1 except that the amount of sodium metaperiodate was changed to 0.6 g, the oxidation reaction temperature was changed to 4° C. and the amount of sodium borohydride was changed to 0.2 g, to obtain 1.65 g of an intended polysaccharide polyol.

The properties of the polysaccharide polyol were as described below.

Elementary Analysis Values:
C: 43.6%

H: 6.0%

Molecular Weight:

The molecular weight was similar to that of the polysaccharide obtained in Example 1.

Structure:

The polysaccharide polyol consisted of the first, second and third recurring units of the formulae (I), (II) and (III), and per 100 of the sum of the first, second and third recurring units, the number of the third recurring units was about 7, the number of the sum of the second and third recurring units was 21, the number of the sum of the groups of the formulae (A) and (C) was about 21 and the number of the sum of the groups of the formulae (B) and (D) was about 7.

EXAMPLE 3

To 300 ml of distilled water was added 2 g of the parent polysaccharide prepared in Example 1, and the mixture was sufficiently stirred. Then, 0.4 g of sodium metaperiodate was added to the mixture and reaction was carried out at 4° C. with stirring for 8 days under insulation of light. Then, 0.5 ml of ethylene glycol was added to the reaction mixture and the mixture was stirred for 3 hours. Then, 200 ml of distilled water was added and the pH value was adjusted to 8.0 by addition of an aqueous sodium hydrogen carbonate solution having a concentration of 0.5 mole/l. Then, 0.25 g of sodium borohydride was added and the mixture was stirred for 1 day. Then, a small amount of acetic acid was added to the reaction liquid to adjust the pH value to 6.0. The solution was dialyzed for 5 days by using distilled water as the external liquid. The internal liquid was freeze-dried to obtain 1.70 g of an intended polysaccharide polyol.

The properties of the polysaccharide were as described below.

Elementary Analysis Values:

C: 43.5%

H: 6.1%

Molecular Weight:

The molecular weight was similar to that of the polysaccharide obtained in Example 1.

Structure:

The polysaccharide polyol consisted of the recurring units of the formulae (I), (II) and (III), and per 100 of the sum of the first, second and third recurring units, the number of the third recurring units was about 7, the number of the sum of the second and third recurring units was about 21, the number of the sum of the groups of the formulae (A) and (C) was about 11 and the number of the sum of the groups of the formulae (B) and (D) was about 17.

EXAMPLE 4

A parent polysaccharide was prepared in the same manner as described in Example 1 except for excluding the addition of cetyl pyridinium chloride and the subsequent centrifugal separation. In 400 ml of distilled water was dispersed 2 g of the thus-prepared polysaccharide, and oxidation reaction was carried out by using 1.3 g of potassium metaperiodate in the same manner as described in Example 1. The subsequent treatment were carried out in the same manner as described in Example 1 to obtain 1.6 g of an intended polysaccharide polyol.

The properties of the polysaccharide polyol were as described below.

Elementary Analysis Values:

C: 43.2%

H: 5.9%

Molecular Weight:

The molecular weight was similar to that of the polysaccharide polyol obtained in Example 1.

Structure:

The polysaccharide polyol consisted of the first, second and third recurring units of the formulae (I), (II) and (III), and per 100 of the sum of the first, second and third recurring units, the number of the third recurring units was about 6, the number of the sum of the second and third recurring units was 20, the number of the sum of the groups of the formulae (A) and (C) was about 24 and the number of the sum of the groups of the formulae (B) and (D) was about 2.

EXAMPLE 5

A parent polysaccharide was prepared in the same manner as described in Example 4. Then, 2 g of the polysaccharide was oxidized and reduced in the same manner as described in Example 1. After completion of the reduction reaction, a small amount of acetic acid was added to the reaction mixture to adjust the pH value to 6.0 and the mixture was subjected to an ultrasonic irradiation treatment under conditions of 20 KHz and 100 W with stirring for 30 minutes while the mixture was cooled from the outside.

Then, acetone in an amount 2 times the amount of the treated liquid was gradually added to the treated liquid while being stirred, and then the mixture was subjected to centrifugal separation. The supernatant was removed, and the precipitate was dissolved in 300 ml of distilled water and dialysis was carried out for 5 days. The internal liquid was freeze-dried to obtain 1.60 g of a white intended polysaccharide polyol.

The properties of the polysaccharide polyol were as described below.

Elementary Analysis Values:

C: 43.2%

H: 6.0%

Molecular Weight:

When gel permeation high pressure liquid chromatography was carried out under the same conditions as described in Example 1, the polysaccharide polyol was eluted at the position of the retention time of a molecular weight of about 120,000.

Structure:

The polysaccharide polyol consisted of the first, second and third recurring units of the formulae (I), (II) and (III), and per 100 of the sum of the first, second and third recurring units, the number of the third recurring units was about 6, the number of the sum of the second and third recurring units was about 19, the number of the sum of the groups of the formulae (A) and (C) was about 21 and the number of the sum of the groups of the formulae (B) and (D) was about 4.

EXAMPLE 6

The steps precedent to the aqueous alkaline solution extraction were conducted in the same manner as described in Example 1, and the aqueous alkaline solution extraction was carried out in the same manner as described in Example 1 except that the extraction temperature was changed to 20° C. The pH value of the extract was adjusted to 6.5 by addition of hydrochloric acid, and in the same manner as described in Example 1, an aqueous cetyl pyridinium chloride solution (10%) was added to the solution and the formed precipitate was removed by centrifugal separation. The supernatant was dialyzed in running water for 2 days, and the internal liquid was concentrated under reduced pressure at 40° C. until the volume was reduced to 3 liters. Then, methanol in a volume equal to the volume of the concentrate was added to the concentrate and the formed precipitate was recovered by centrifugal separation conducted under 10,000 G for 30 minutes. The recovered precipitate was added to 300 ml of methanol, and the mixture was stirred for about 1 hour and subjected to centrifugal separation to obtain a precipitate. This methanol washing was further conducted 2 times, and the obtained precipitate was dried under reduced pressure to obtain 10.5 g of a parent polysaccharide.

The thus-obtained polysaccharide was analyzed in the same manner as described in Example 1.

Elementary Analysis Values:
C: 44.31%
H: 6.10%
N: below detection limit
Molecular Weight:

The polysaccharide was eluted at the position of the retention time of a molecular weight of about 550,000.

Molar Ratios of Methylated Saccharides:
2,3,4,6-tetra-0-methylglucose: 1
2,4,6-tri-0-methylglucose: 4.26
2,3,4-triO-methylglucose: 0.32
2,4-di-0-methylglucose: 1.01

The molar ratio between glucose and gentiobiose obtained by digestion by an exo-type $\beta$-1,3-glucanase was 1/0.160.

Ratios of Recurring Units:
The number of the recurring units of the formulae (V) was 6 per 100 of the total recurring units, and the number of the sum of the recurring units of the formulae (IV) and (V) was 19 per 100 of the total recurring units.

The other analysis results were substantially the same as those obtained in Example 1.

By using 2 g of the thus-obtained parent polysaccharide, the oxidation reaction treatment and subsequent treatments were carried out in the same manner as described in Example 1 to obtain 1.6 g of an intended polysaccharide polyol.

Elementary Analysis Values:
C: 43.9%
H: 6.1%
Molecular Weight:

The polysaccharide polyol was eluted at the position of the retention time of a molecular weight of about 500,000.

Structure:
The polysaccharide polyol consisted of the first, second and third recurring units of the formulae (I), (II) and (III), and per 100 of the sum of the first, second and third recurring units, the number of the third recurring units was about 6, the number of the sum of the second and third recurring units was 19, the number of the sum of the groups of the formulae (A) and (C) was 23 and the number of the sum of the groups of the formulae (B) and (D) was 2.

EXAMPLE 7 (WATER SOLUBILITY TEST)

The parent polysaccharide obtained in Example 1 and the polysaccharide polyols obtained in Examples 1 through 6 were precisely weighed. Then, 50 ml of physiological saline solution (having a pH value of 6.3) was added to each sample and the mixture was stirred at 40° C. for 3 hours. The obtained results are shown in Table 1. When purified water (having a pH value of 6.7) was used instead of the physiological saline solution, similar results were obtained.

From the results shown in Table 1, it is apparent that the solubility of the polysaccharide of the present invention in the neutral region is highly improved.

TABLE 1

| Sample | Amount (mg) | State of Liquid |
|---|---|---|
| Parent polysaccharide of Example 1 | 100 | Polysaccharide was suspended and dissolved state was not observed |
| Parent polysaccharide of Example 1 | 20 | Polysaccharide was suspended and dissolved state was not observed |
| Polysaccharide polyol obtained in Example 1 | 100 | Uniformly dissolved to give viscous solution |
| Polysaccharide polyol obtained in Example 2 | 100 | Uniformly dissolved to give viscous solution |
| Polysaccharide polyol obtained in Example 3 | 100 | Uniformly dissolved to give viscous solution |
| Polysaccharide polyol obtained in Example 4 | 100 | Uniformly dissolved to give viscous solution |
| Polysaccharide polyol obtained in Example 5 | 100 | Uniformly dissolved |
| Polysaccharide polyol obtained in Example 5 | 500 | Uniformly dissolved |
| Polysaccharide polyol obtained in Example 6 | 100 | Uniformly dissolved to give viscous solution |

EXAMPLE 8 (ANTI-TUMOR TEST USING Sarcoma 180 and ICR Mice

About 6,000,000 of Sarcoma 180 tumor cells collected after 6 days' incubation in the abdominal cavity were implanted subcutaneously into the region covering the right groin to the back of the 6-weeks-old healty female ICR mice having a body weight of 23 g. For 10 days from the next day, a solution of the polysaccharide polyol of the present invention in physiological saline solution or a suspension of the starting polysaccharide in physiological saline solution (comparison) was injected intraperitoneally once a day. In the control group, no treatment was carried out.

When 5 weeks had passed from the day of transplantation, the tumor was extracted surgically and the weight was measured. Simultaneously, the number of mice which had completely regressed was counted.

The tumor inhibition ratio was calculated according to the following formula:

$$\text{Tumor inhibition ratio (\%)} = \frac{\overline{C} - \overline{T}}{\overline{C}} \times 100$$

wherein $\overline{C}$ is the average tumor weight in the control group and $\overline{T}$ is the average tumor weight of the administered group. The obtained results are shown in Table 2. It is seen that the polysaccharide polyol of the present invention has an improved anti-tumor effect, especial in the low administration rate region.

TABLE 2

| Sample | Dose (mg/kg/day) | Average Tumor Weight (g) | Tumor Inhibition Ratio (%) | Complete Regression |
|---|---|---|---|---|
| Polysaccharide polyol of Example 1 | 1 | 0 | 100 | 8/8 |
| | 5 | 0 | 100 | 8/8 |
| Polysaccharide polyol of Example 2 | 1 | 0 | 100 | 8/8 |
| | 5 | 0.1 | 98.7 | 7/8 |
| Polysaccharide | 1 | 0.2 | 97.4 | 7/8 |

TABLE 2-continued

| Sample | Dose (mg/kg/day) | Average Tumor Weight (g) | Tumor Inhibition Ratio (%) | Complete Regression |
|---|---|---|---|---|
| polyol of Example 3 | | | | |
| Polysaccharide polyol of Example 4 | 1 | 0 | 100 | 8/8 |
| Polysaccharide polyol of Example 5 | 1 | 0.1 | 98.7 | 7/8 |
| Polysaccharide polyol of Example 6 | 1 | 0 | 100 | 8/8 |
| | 5 | 0 | 100 | 8/8 |
| Control | — | 7.6 | — | 0/8 |
| Comparison 1 (parent polysaccharide of Example 1) | 1 | 0.4 | 94.7 | 6/8 |
| | 5 | 0.1 | 98.7 | 7/8 |
| Comparison 2 (parent polysaccharide of Example 6) | 1 | 0.5 | 93.4 | 6/8 |
| | 5 | 0.0 | 100 | 8/8 |

Example 9 (Anti-Tumor Test Using Sarcoma 180 and C3H/He Mice)

The anti-tumor test was carried out by using female C3H/He mice having a body weight of about 23 g in the same manner as described in Example 8. The results are shown in Table 3. It is seen that the polysaccharide of the present invention is effective as an anti-tumor agent.

TABLE 3

| Sample | Dose (mg/kg/day) | Average Tumor Weight (g) | Tumor Inhibition Ratio | Complete Regression |
|---|---|---|---|---|
| Polysaccharide polyol of Example 1 | 1 | 1.0 | 85.7 | 5/8 |
| | 5 | 2.1 | 70.0 | 3/8 |
| Polysaccharide polyol of Example 2 | 1 | 1.9 | 72.8 | 3/8 |
| Polysaccharide polyol of Example 5 | 1 | 1.1 | 84.3 | 5/8 |
| Polysaccharide polyol of Example 6 | 1 | 1.2 | 82.9 | 5/8 |
| | 5 | 1.5 | 78.6 | 3/8 |
| Control | — | 7.0 | 0 | 0/8 |
| Comparison 1 (Parent polysaccharide of Example 1) | 1 | 3.1 | 55.7 | 0/8 |
| | 5 | 2.7 | 61.4 | 0/8 |
| Comparison 2 (Parent polysaccharide of Example 6) | 1 | 2.8 | 60.0 | 0/8 |
| | 5 | 2.6 | 62.9 | 1/8 |

We claim:

1. A polysaccharide polyol derived from *Volvariella volvacea*, which consists essentially of first recurring units represented by the following formula:

wherein D-Glu represents a D-glucopyranosyl group, β represents the linkage mode and each number represents the linkage position, second recurring units represented by the following formula:

wherein D-Glu, β and each number are defined above, and X represents a group represented by the following formula:

or a D-glucopyranosyl group represented by the following formula:

and third recurring units represented by the following formula:

wherein D-Glu, β and each number are defined above, and Y represents a group represented by the following formula:

or a D-glucopyranosyl residue represented by the following formula:

in each formula, X being linked to the carbon atom to which (P) is attached and the group being linked to the glucopyranosyl residue through the oxygen atom to which (Q) is attached, wherein a part of X, in at least one of the second recurring units and the third recurring units is a group represented by the following formula:

the average number of the third recurring units is about 4 to about 12 per 100 of the sum of the first, second and third recurring units, and the average number of the sum of the second and third recurring units is about 16 and about 33 per 100 of the sum of the first, second and third recurring units, said polysaccharide polyol having a molecular weight of about 70,000 to about 2,800,000 in gel permeation high speed liquid chromatography using as the mobile phase a tris-hydrochloride buffer solution having a concentration of 0.1 mole/l and a pH value of 8.6.

* * * * *